US010783448B2

(12) United States Patent
Shklarski et al.

(10) Patent No.: US 10,783,448 B2
(45) Date of Patent: Sep. 22, 2020

(54) EXTRACTING FACTS FROM UNSTRUCTURED DATA

(71) Applicant: Flatiron Health Inc., New York, NY (US)

(72) Inventors: Gil Shklarski, New York, NY (US); Amy Abernethy, Cary, NC (US); Benjamin Birnbaum, Brookyln, NY (US); Geoffrey Calkins, Brooklyn, NY (US); Dominique Connolly, Jersey City, NJ (US); Joseph Delgado, New York, NY (US); Joseph DiLallo, Bethpage, NY (US); James Dura, New York, NY (US); Daniel Eisenberg, New York, NY (US); Lauren Ellsworth, Brooklyn, NY (US); Ross Feinstein, New York, NY (US); Jeremy Feinstein, New York, NY (US); Caitlin Keenan, New York, NY (US); Jeremy Kohansimeh, New York, NY (US); Dennis Lee, New York, NY (US); Elijah Meerson, Brooklyn, NY (US); Catherine Miller, New York, NY (US); Joseph Mou, Brooklyn, NY (US); Nathan Nussbaum, Millburn, NJ (US); Cynthia Revol, Dallas, TX (US); Paul Richardson, New York, NY (US); Maayan Roth, Brooklyn, NY (US); Melisa Tucker, Brooklyn, NY (US); Nathaniel Turner, New York, NY (US); Zachary Weinberg, New York, NY (US); Paul You, Brooklyn, NY (US)

(73) Assignee: FLATIRON HEALTH, INC., New York, NY (US)

( * ) Notice: Subject to any disclaimer, the term of this patent is extended or adjusted under 35 U.S.C. 154(b) by 742 days.

(21) Appl. No.: 15/211,250

(22) Filed: Jul. 15, 2016

(65) Prior Publication Data
US 2017/0039341 A1 Feb. 9, 2017

Related U.S. Application Data

(60) Provisional application No. 62/202,597, filed on Aug. 7, 2015.

(51) Int. Cl.
*G06N 20/00* (2019.01)
*G16H 50/70* (2018.01)

(52) U.S. Cl.
CPC .............. *G06N 20/00* (2019.01); *G16H 50/70* (2018.01)

(58) Field of Classification Search
CPC .......... G06N 20/00; G06N 5/022; G06N 5/04; G06N 7/005; G06N 5/02; G06N 3/006;
(Continued)

(56) References Cited

U.S. PATENT DOCUMENTS 5,664,109 A 9/1997 Johnson et al.
5,974,389 A 10/1999 Clark et al.
(Continued)

*Primary Examiner* — Paulinho E Smith
(74) *Attorney, Agent, or Firm* — Finnegan, Henderson, Farabow, Garrett & Dunner LLP

(57) ABSTRACT

Methods, systems, and apparatus, including computer programs encoded on computer storage media, to present a video. One of the methods includes obtaining one or more unstructured documents. The method includes obtaining, by a computer system, a data model, the data model identifying a type of fact that can be determined from the one or more unstructured documents. The method includes determining, by the computer system, a channel to extract facts from the document based on the type of fact. The method includes distributing, by the computer system, the one or more
(Continued)

unstructured documents to the channel. The method includes extracting, by the channel, facts from the one or more unstructured documents. The method also includes storing the facts in a data model.

25 Claims, 8 Drawing Sheets

(58) Field of Classification Search
CPC .......... G06N 3/04; G06N 3/0472; G06N 3/08; G06N 5/003; G06N 7/08; G06Q 30/0631; G06Q 30/0282; H04L 67/22; H04N 21/251; H04N 21/4668; H04N 21/4756
See application file for complete search history.

(56) References Cited

U.S. PATENT DOCUMENTS

| | | |
|---|---|---|
| 6,912,549 B2 | 6/2005 | Rotter et al. |
| 7,624,027 B1 | 11/2009 | Stern et al. |
| 2004/0243545 A1 | 12/2004 | Boone et al. |
| 2009/0006131 A1 | 1/2009 | Unger et al. |
| 2010/0094657 A1 | 4/2010 | Stern et al. |
| 2014/0025429 A1* | 1/2014 | Nihal ............... G06Q 10/06311 705/7.32 |
| 2016/0048655 A1* | 2/2016 | Maitra ............... G06F 19/3456 705/3 |
| 2016/0224662 A1* | 8/2016 | King ............... G06F 16/951 |

* cited by examiner

EXTRACTING FACTS FROM UNSTRUCTURED DATA

BACKGROUND

A medical record is a systematic documentation of a patient's medical history and care across time within a particular health care provider. The medical record includes a variety of types of "notes" entered over time by health care professionals, recording observations and administration of drugs and therapies, orders for the administration of drugs and therapies, test results, x-rays, reports, etc. The maintenance of complete and accurate medical records is a requirement of health care providers and is generally enforced as a licensing or certification prerequisite.

SUMMARY

This specification describes technologies relating to fact extraction.

In general, one innovative aspect of the subject matter described in this specification can be embodied in methods that include the actions of obtaining one or more unstructured documents. The methods include the actions of obtaining, by a computer system, a data model, the data model identifying a type of fact that can be determined from the one or more unstructured documents. The methods include the actions of determining, by the computer system, a channel to extract facts from the document based on the type of fact. The methods include the actions of distributing, by the computer system, the one or more unstructured documents to the channel. The methods include the actions of extracting, by the channel, facts from the one or more unstructured documents. The methods also include the actions of storing the facts in a data model.

Other embodiments of this aspect include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The foregoing and other embodiments can each optionally include one or more of the following features, alone or in combination. Extracting facts may be performed by a computer system. A method may include the actions of verifying the facts stored in the data model, wherein the one or more unstructured documents include training documents for which the facts are known. A method may include the actions of identifying a cohort of patients based on the extracted facts. A method may include the actions of determining a measure of quality for the extracted facts and updating the data model based on the measure of quality. The methods may include the actions of identifying an extracted fact as being longitudinal and comparing the extracted fact to previously extracted facts of the same type for the same patient. The methods may include the actions of extracting a set of facts from a set of unstructured documents, establishing the set of unstructured documents as a training set, training a model using the set of facts and the set of unstructured documents, and extracting new facts from new unstructured documents using the model.

Particular embodiments of the subject matter described in this specification can be implemented so as to realize one or more of the following advantages. The usefulness of electronic medical records can be increased. The system helps adjudicate relevant information that may conflict to best represent real world occurrence. Patients can be identified as members of a cohort with specific properties by combining structured information with unstructured information.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Patient-related Information can be recorded in a variety of formats in an electronic medical record (EMR). For example, a health care provider (HCP) may interact with a patent, for example, during a routine checkup, diagnosis of specific ailment, hospital stay, etc. The HCP may record information from an interaction between a health care provider and a patient in the free-text notes. The free-text notes may include observations made by the HCP, results of a diagnostic, a description of a treatment choice, or other statements and conclusions related to that interaction. Because free-text notes can include information on any topic and in any format, they are generally unstructured and the format is not standardized. The unstructured information is difficult to query, analyze, and interpret programmatically. Other examples of unstructured information include reports not generated by a clinician and lab results.

Even when data is largely structured, components of the data may be unstructured. For example, a field in a table or report may include free text or may include content for which the semantics or structure are unknown. Structured data can also become unstructured due transmission methods. For example, a spreadsheet that is faxed or turned into a read only text document (such as a PDF) loses much of its structure.

A system can transform unstructured information recorded as a result of a patient interaction into a form that is more regular, and thereby improving its utility. In some implementations, documents including unstructured data can be processed to generate structured data. The content of documents containing the unstructured information can be processed and the content can be stored as structured information.

Figure 1:
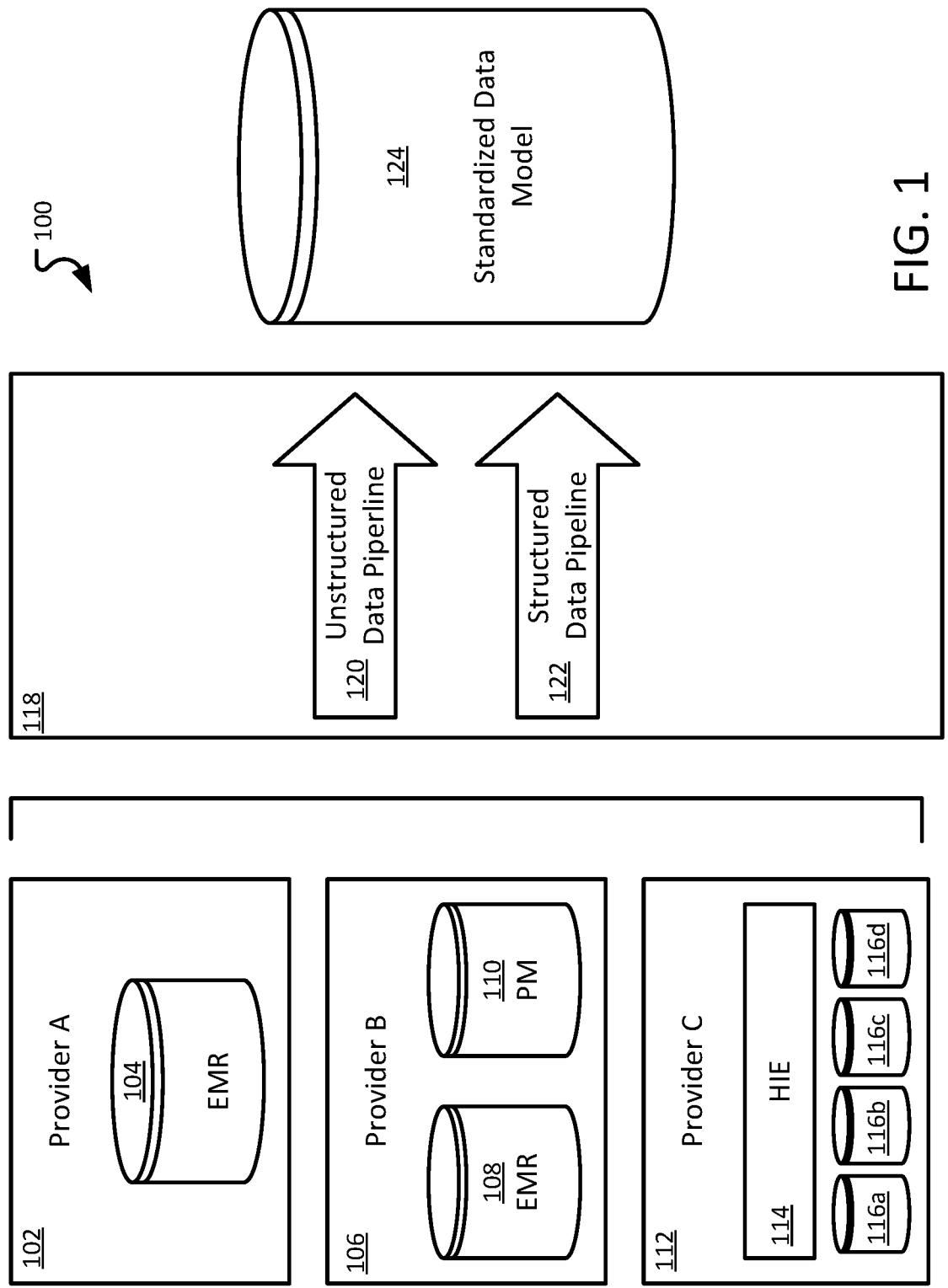
FIG. 1 illustrated an exemplary system for converting patient data stored in disparate systems into a standardized data model.

FIG. 1 illustrates an exemplary system for converting patient data stored in disparate systems into a standardized data model. Patient related information can be stored in different formats. Frequently, the format of the information is dependent on the provider. For example, some medical services providers, represented in FIG. 1 by Provider A 102, may store patient-related information in electronic medical record software (EMR) 104. Some medical service providers, represented in FIG. 1 by Provider B 106, may store information in a combination of EMR 108 and a practice management system (PM) 110. Some medical provides, represented in FIG. 1 by Provider C 112, may store patent information in a health information exchange (HIE) 114, which in turn stores patient-related information in one or more databases 116a-d.

A patient-related information pipeline system 112 can obtain data from disparate providers and transform the patient-related information into a standardized data model 124. The patient-related information pipeline system 112 can include multiple different pipelines based on the source of the patent information. In general, the pipelines can be divided into two different categories. Pipelines that process unstructured data, represented in FIG. 1 by the Unstructured Data Pipeline 120, and pipelines that process structured data, represented in FIG. 1 by the Structured Data Pipeline 122. In used herein, a pipeline refers to a system that manages the movement and transformation of data. The pipeline may define a data-driven workflow that defines a series of tasks that need to be performed successfully in a predetermined order. The pipeline may also identify tasks or a series of tasks that can be performed in parallel.

Structured pipelines obtain facts that are identified in the structure of the document and transfer those facts into fields in a data model. In some scenarios, the pipeline may alter the data type or format of the data. For example, the pipeline may convert a string to a number or may alter the format of a date into a standard format.

The processing of the patient-related information can be performed in a HIPAA (The Health Insurance Portability and Accountability Act) compliant manner.

Figure 2:
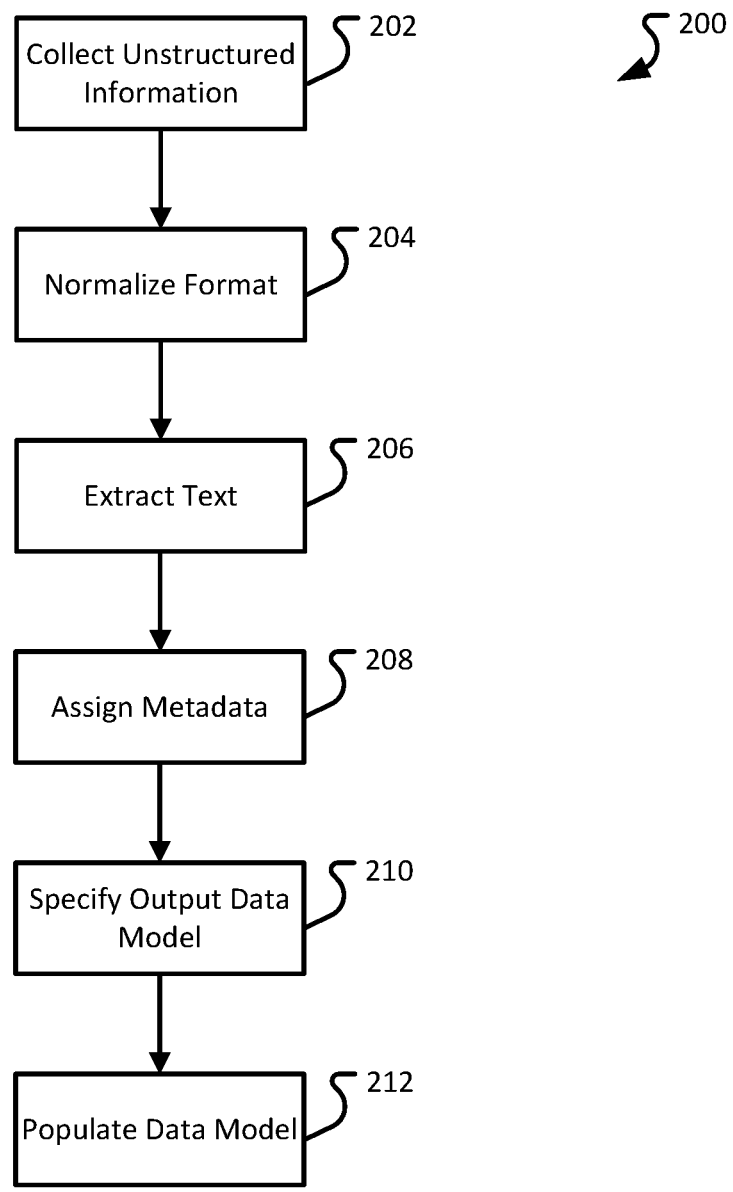
FIG. 2 illustrates an exemplary process for processing unstructured data.

FIG. 2 illustrates an exemplary process 200 for processing unstructured data. The process may be managed by a computer system, for example, the patent information pipeline system 112 of FIG. 1. For simplicity, the steps in the process are described as being performed by the process, however, the steps in the process can be performed, for example, by a general purpose or specialized computer executing a data processing pipeline.

The process 200 collects unstructured information 202. Documents containing unstructured information are collected. These documents may have been collected from disparate data sources, as described above with respect to FIG. 1. The documents contain facts about patient-related information that can be extracted. The unstructured information may be collected by automated agents.

As described above, unstructured document are documents where the syntactic structure of the payload of the document is not predetermined. The payload of the document (sometimes referred to as the actual or body data) is part of the document which is the fundamental purpose of the document or the part of the document that is ordinarily displayed when the document is rendered to a viewer, to the exclusion of information sent with the payload (such as headers or metadata, sometimes referred to as overhead data). For example, an electronic free-text note may be identified as a note, may identify who created the note, may identify when the note was created, but does not include any syntactic information about the contents (payload) of the note. In some implementations, an unstructured document is a document that includes only basic elements such as shapes (e.g. graphics), images (e.g. bitmaps), video, and glyphs (e.g. letters, numbers, and punctuation marks). The unstructured document may not specify a relationship of association between the basic elements of the document. In some scenarios the document may identify grammatical relationships between the basic elements, for example, glyphs may be organized into words, sentences, and paragraphs. However, in general, the unstructured document does not ascribe additional context to at least a portion of the contents of the unstructured document beyond the identity of the document itself (e.g. doctor's note). In some implementations, the unstructured document may be associated with metadata, for example, the type of document, the origin of the document, a date the document was created, the name and/or job of the person who created the document, etc . . . .

In contrast, a structured document may include a payload that includes tags, fields, or other information built into the data structure of the document that provides additional context to the document (e.g., a name field that includes the patient's name).

The process 200 normalizes the format of the unstructured documents 204. Each unstructured document may be converted into a standard format. For example, text documents may be converted into EBSIDIC or ASCII flat files, or word processor documents. Images may be converted into a portable network graphics file (PNG), a graphics interchange format file (GIF), or a Joint Photographic Experts Group File (JPEG).

The process 200 extracts text 206 from the standard format document. Text from text documents may be parsed. Image files may be processed using optical character recognition (OCR) and handwriting analysis programs and techniques. Embedded text can be extracted.

The process 200 assigns metadata to the document 208. The document may be tagged with a category identifier that generally identifies the type of document received. For example, a lab report from a pathologist may be identified as a pathology report.

Tags and additional metadata can be identified using machine learning processes. In general, machine learning algorithms make predictions about data based on a model created from example. For example, a group of training documents can be collected. Tags and/or metadata is assigned to each of the training documents. A model can be created by providing the training documents through a machine learning algorithm. For example, a collection of training document may be tagged with a "physician diagnosis" tag. A machine learning system generates a model based on the training documents. Subsequently, the model can be used to determine whether new documents should be tagged with the "physician diagnosis" tag.

The normalized documents can be provided to a trained model. The model compares the provided document to data derived from the training documents and can determine meta-data based, at least in part, on the similarity between the normalized document and the training documents.

The process 200 specifies the output data model 210. The unstructured document pipeline may select a data model that defines a structured data format to be used when processing the unstructured data. The data model may be selected for the collection of unstructured data by a content author or another user responsible for the generation of the structured content. In some scenarios, a new data model may be generated for the structured content, as described below with respect to FIG. 5.

The process 200 can populate the data model with information from the unstructured documents 212. Facts contained within the unstructured documents are extracted and stored in the data model. The process of extracting facts from the unstructured document is explained further below.

Figure 3:
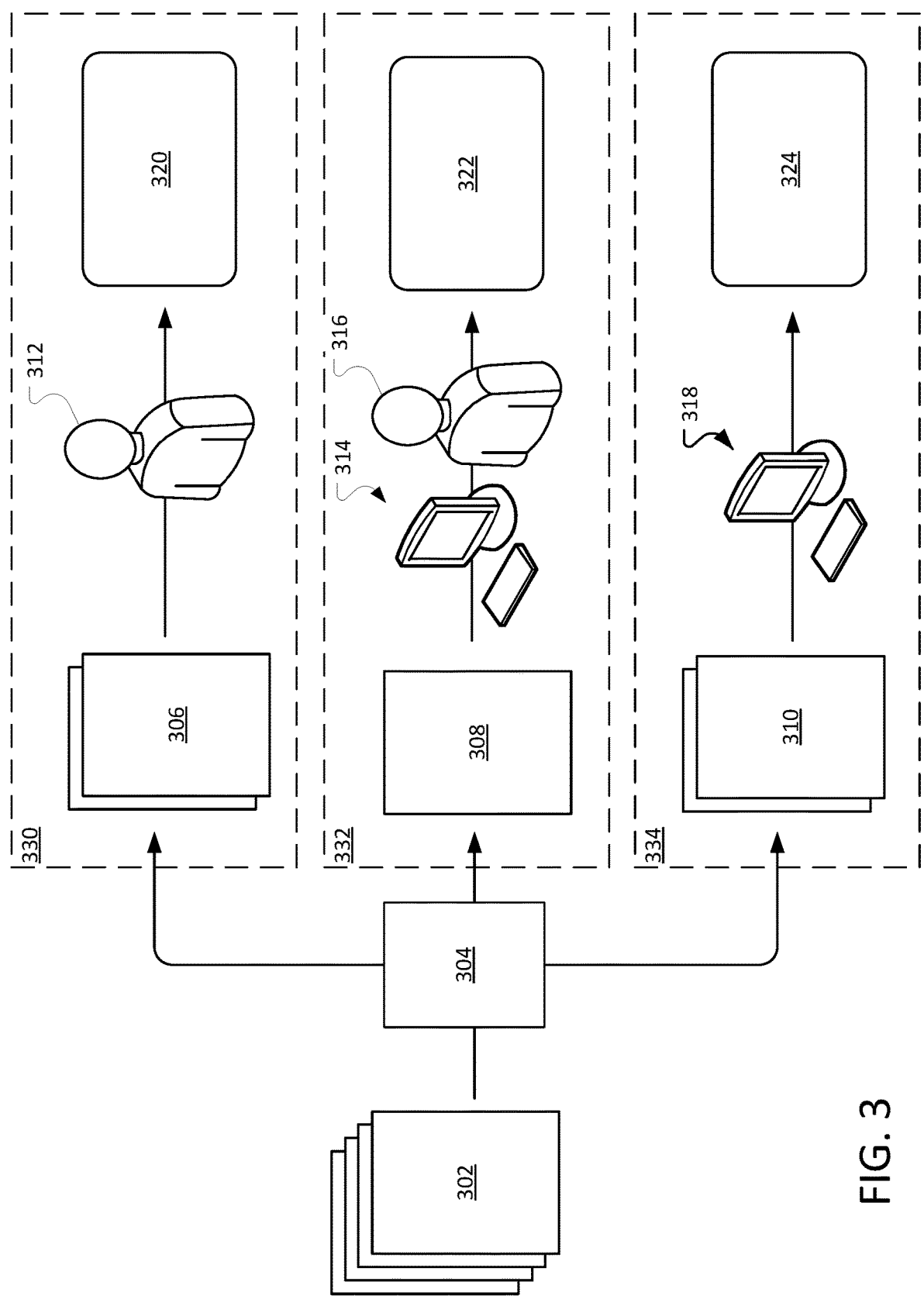
FIG. 3 illustrates an example of populating the data model with information from the unstructured documents.

FIG. 3 illustrates an example of populating the data model with information from the unstructured documents 302. A controller 304 determines, per specifications of a project coordinator/operator, which pieces of input data are shown to which abstractors to collect which pieces of output data using a particular behavior of the web-based application. The controller 304 may include a user interface and input device that enables a project coordinator to define the parameters for the populating the data model. A project coordinator can define the qualifications necessary to extract different types of facts (e.g., an oncology expert, a registered nurse, a student, etc . . . ). The project coordinator can also identify a channel for the particular type of fact. For example, a channel may be determined based on whether a type of fact can be extracted by automated computer processes, by automated computer processes with confirmation by a human abstractor, or by a human abstractor. The project coordinator can define a level of confidence or quality for each element in the data model.

In some implementations, a project may be generated for training or testing purposes. For example, unstructured training documents with previously determined facts may be processed to train new human abstractors, to test the reliability of the automated computer processes, or to evaluate human abstractors. The project coordinator can define whether the data is being processed for training or testing purposes. In general, training refers to a process that ensure consistency in output data across human abstractors given a particular set of unstructured documents and operational specifications. Testing refers to the process of validating the training process before relying on any output data produced by the system. Human abstractors who perform well during the testing may be identified as expert abstractors.

The project coordinator can identify fields in the data model that can be processed using a computer system, fields that require confirmation by a human abstractor, and fields that need to be processed by a human abstractor. The project coordinator can identify if the type of facts in the unstructured document that pertain to a field or fields in longitudinal data, that is, data that tracks the same variables over a period of time (e.g., tumor size).

In some implementations, a particular project may be part of a research study that occurs over a long period of time. The operator may be able to identify subscription data, or data that tracks the progress of a single patient over time. This enables a project to continuously learn about that patient over time, and to have the best known information as it pertains to that patient at any given time in the patient's history.

The controller 304 divides the unstructured documents based on the appropriate channel for the type of facts that are to be extracted from the document. Unstructured documents pertaining to an individual do not need to be delivered to the same channel. A patient's medical record may be divided into multiple smaller pieces of unstructured data and distributed to different channels, or to different processors within a channel. For example, a free-text note about a patient may be distributed separately from a graph showing the patients progression over time.

Generally, the documents may be divided for processing by multiple channels. Channel 330 includes documents 306 that include types of facts that need to be determined by a human abstractor 312. The human abstractor 312 receives the necessary documents, reviews the documents, and stores the facts in a data model 320. Multiple channels provide an upgrade path. For example, initially facts may be extracted by a human abstractor. As the number of extracted facts are collected, training documents can be created and used to train a model using machine learning algorithm. Then, for a time, facts extracted by computers using the model may be verified by human abstractors. Once the quality of the facts extracted by the computers using the model is sufficiently high, the facts may be extracted by the computer using the model subsequent verification.

Channel 332 includes documents 308 that include types of facts that can be determined using human assisted computer technology. For example, the facts may be extracted using regular expressions or machine learning techniques (as described above.) A computer system 314 receives the documents 308 and identifies facts from the document. The documents and facts are then provided to a human abstractor 316 to verify that the facts were appropriately derived from the documents. If the human abstractor 316 verifies that the facts were appropriately derived, for example, by approving the facts on a user interface. The computer system can store the derived facts in the data model 322.

If the human abstractor 316 indicates that the facts were incorrectly derived, in some implementations, the human abstractor 316 may be able to identify the requested facts. In some implementations, the document and the derived facts may be routed to a second abstractor (not shown) to confirm the judgment of the initial human abstractor. In some implementations, the document that was the source of the incorrectly derived fact may be routed for further processing. For example, the document may be moved to the documents 306 that require a human abstractor to identify the facts.

In some scenarios, a human abstractor (e.g., human abstractor 314 and human abstractor 316) may encounter ambiguities in the unstructured data. For example, the fact to be extracted may not be clearly described in the unstructured data. The system can provide a facility whereby abstractors can collaborate to resolve the ambiguities.

Channel 334 includes documents 310 that include facts that can be determined using computer technology with sufficient reliability that the facts do not need to be verified by a human abstractor. The documents 310 are processed by a computer system 318. Facts can be identified using, for example, models trained using machine learning algorithms. The identified facts are stored in the data model 324.

In some implementations, the system is able to selectively collect facts based on previous information. Facts that are unlikely to change are not collected over multiple time periods, in contrast, longitudinal facts collect only the changed or marginal facts about that patient are collected for the given time period.

Figure 4:
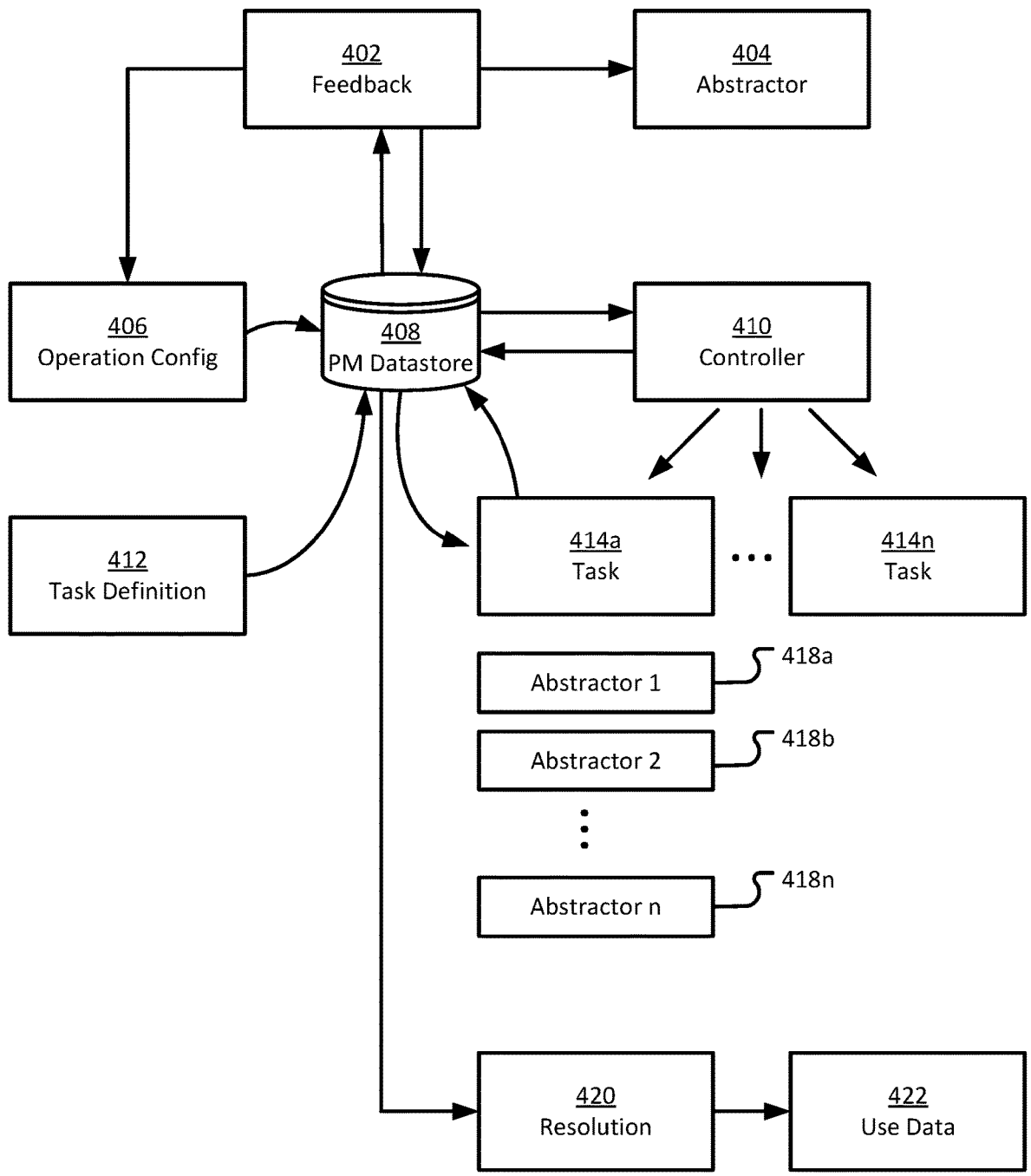
FIG. 4 illustrates an example system for extracting facts from electronic medical records.

FIG. 4 illustrates an example system framework for extracting facts from electronic medical records. The framework enables the creation of projects that identify facts to be extracted from unstructured documents.

The PM Data store 408 serves as a central repository for structured and unstructured documents.

The task definition 412 identifies information about a task. The task definition may define, for example, the facts to be derived from the documents and whether or not the derivation can be performed by an expert system executing on a computer.

The controller 410 distributes tasks 414*a-n* to different abstractors 418*a-n*. Multiple abstractors can be assigned to work on the same task. For example, structured documents may be divided and distributed to abstractors to be processed in parallel. Alternatively or additionally multiple abstractors may receive the same document and the results can be compared. As described above, each abstractor may be an expert system executing on a computer (for example, a model trained using a machine learning algorithm).

Facts extracted by the abstractors can be stored in the PM data store. The PM data store can serve as a warehouse of facts. The facts can be used multiple projects across data populations A feedback module 406 enables an abstractor to collaborate with other abstractors 404 to adjudicate ambiguities or other issues that may arise as they extract facts from the unstructured information.

A resolution module 420 can determine which abstractors provided which output facts at which times, with which input information and provide a single view on the output data which is more likely to represent the facts as they actually occurred. The resolution module 420 automatically outputs use data 422 for consumption independent of the data model specified by content authors.

In some implementations, the operation configuration can be used to identify patients as members of a cohort with specific properties. The system identifies the patients by combining structured information with unstructured information. New information about specific patients can be collected to form an accurate cohort according to the semantics associated with previously collected information. The new information collected is generally a function of the semantics of the previous information. A cohort can be studied together to identify common and disparate facts.

Figure 5:
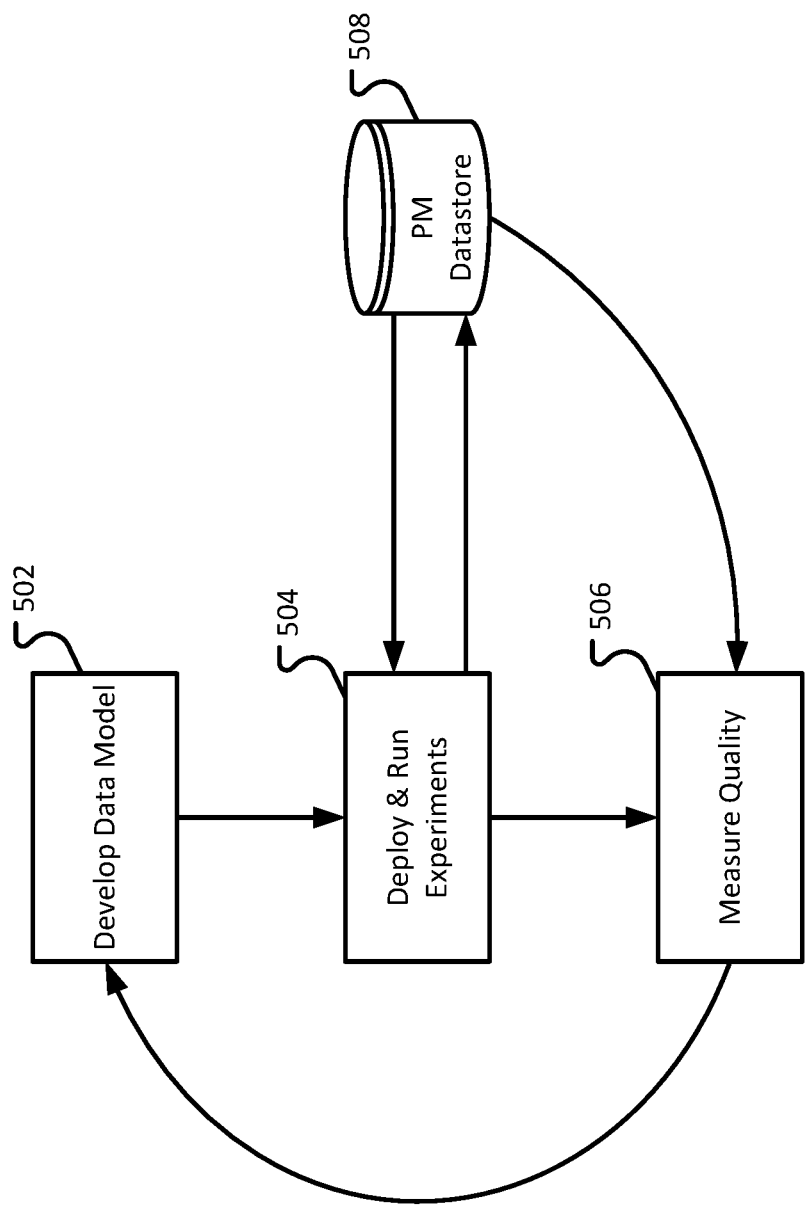
FIG. 5 illustrates an exemplary process for the development of a data model.

FIG. 5 illustrates an exemplary process for development a data model. A user, such as a content author, can define a data model 502 to store facts that are to be extracted from unstructured information. The data model can include, for example, names of output fields, the format of the output fields, and any constraints on the possible values of the output fields. The content author can also describe policies and procedures that are made available to abstractors that abstract the facts from the unstructured data. Content authors are, generally, responsible for understanding and defining the required data structure and may or may not be subject matter experts in other areas (e.g. medicine).

A content author can deploy and run experiments 504. The experiments can be used to measure the quality of efficacy of the data model. An experiment may include, for example, providing the data model and unstructured documents to abstractors. The abstractors analyze the unstructured data using the data model and providing the requested facts. The results of the experiments (e.g., the facts extracted from the unstructured documents) are stored in the PM data store 508.

The results of the experiment can be analyzed and the quality of the results is measured 506. The quality of the results can be compared to an expected quality of results. For example, by testing the data scheme using a training set, as described above. Based on the results of the quality measurement, the content author may further develop and refine the schema 502. Developing a schema, measuring the quality of the data returned, and modifying the schema until the content author is satisfied the schema is able to sufficiently represent and capture real-world data.

Once a schema is developed and deployed such that computer and human abstractors can extract facts from medical records and other documents (as discussed above), it becomes advantageous to be able to schedule tasks, and assign and change priorities in order to effectively and efficiently process the data.

To facilitate the scheduling of tasks, activities can be divided into modules. A module can be considered a set of facts (or types of facts) to be extracted from medical records for a specific population of patients. In some implementations, the module can dictate a subset of the medical records that are provided to the human and computer abstractors in order to obtain the facts. In some implementations, modules may be given a priority ranking. Tasks for modules with a higher priority ranking are generally performed before tasks for modules with a lower priority ranking.

Figure 6:
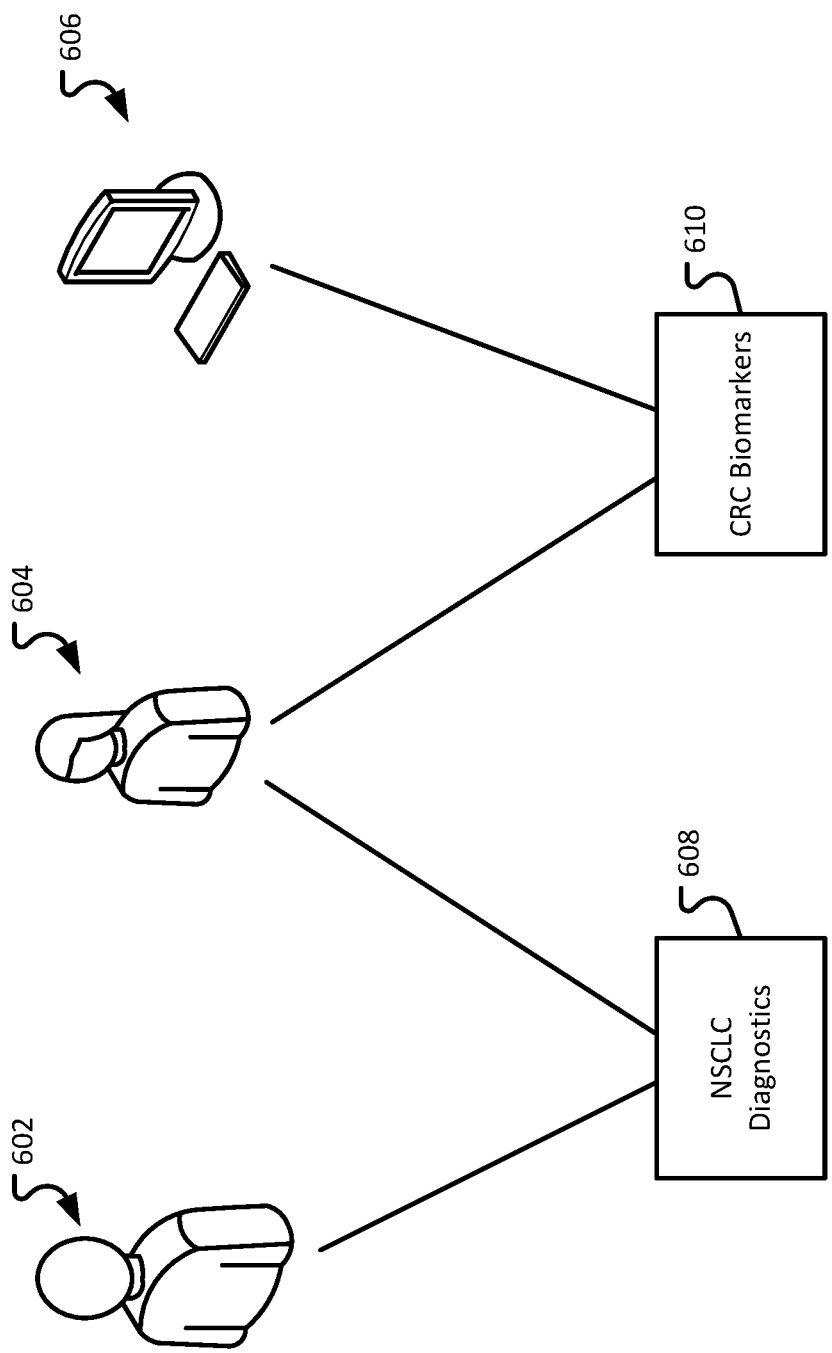
FIG. 6 illustrates an example of abstractors certified to work on different modules.

Abstractors can be granted credentials that dictate which modules they are authorized to work on. For example, referring to FIG. 6, the human abstractor 602 may be credentialed to work on module A 608. The human abstractor 604 may be credentialed to work on module A 608 and module B 610. The computer abstractor 606 may be credentialed to work on module B 610.

Figure 7:
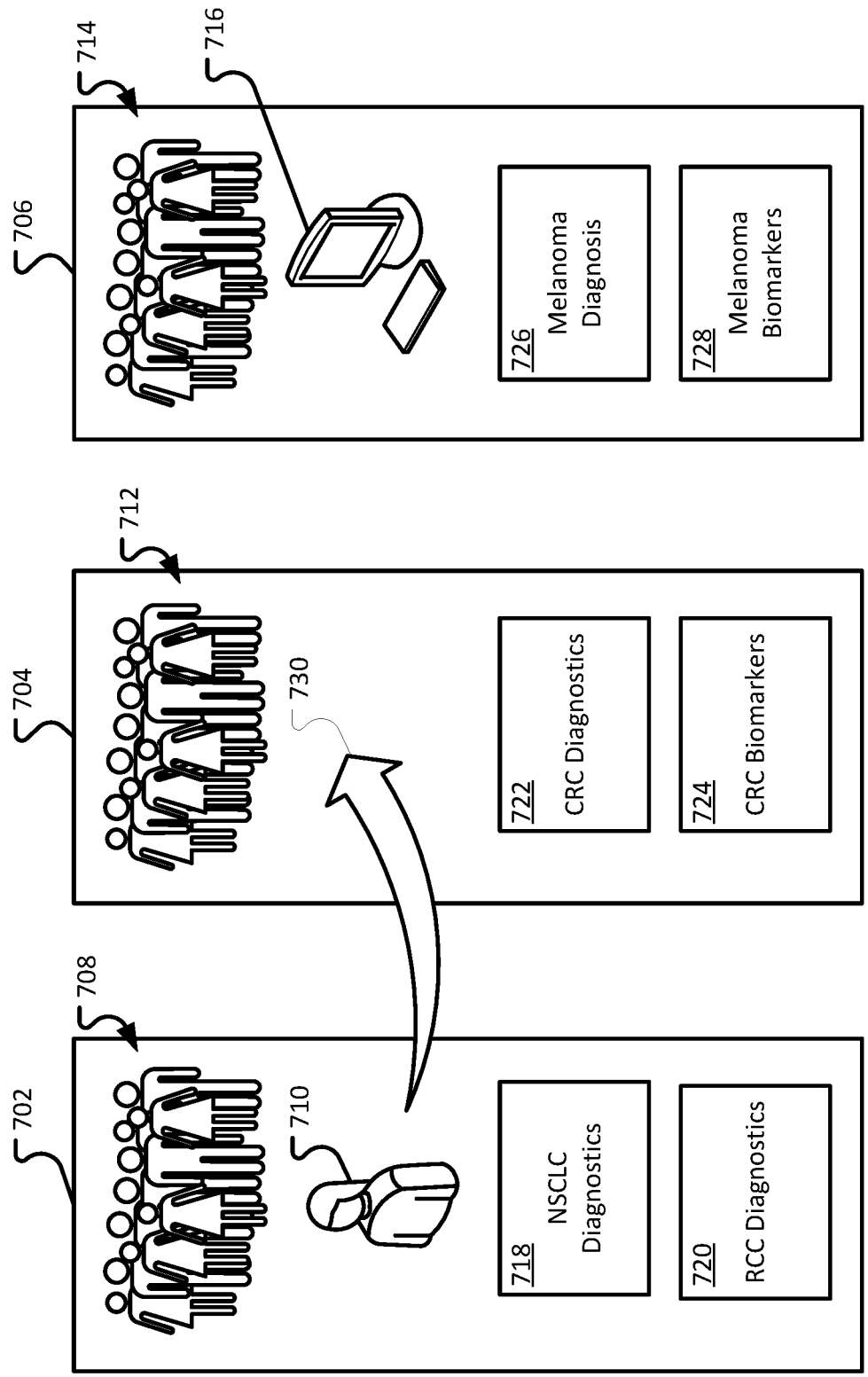
FIG. 7 illustrates an example of segmenting abstractors into home teams.

Abstractors can be divided into teams. Each team can be assigned ownership of a module or set of modules. In some implementations, a module may be owned by only one team. FIG. 7 illustrates an example of segmenting abstractors into home teams. A first team 702 includes a set of abstractors 708 including abstractor 710. A second team 704 includes abstractors 712. A third team includes a set of abstractors 714. While the abstractors 708, 712, and 714 are shown as human abstractors, the set of abstractors can include human, computer, and human verified computer abstractors (for example, the computer extractor 716).

Each team is assigned different modules. In this example, the first team 702 is assigned the NSCLC Diagnostics 718 and the RCC Diagnostics 710 modules. The second team 704 is assigned the CRC Diagnostics 722 and the CRC Biomarkers 724 modules. The third team 706 is assigned the Melanoma Diagnosis 726 and Melanoma Biomarkers 728.

In general, working on tasks for their home team is the primary responsibility of the abstractors. An abstractor may freely work on tasks for any module that is owned by their home team. Note, it is not necessary for a team member to be certified on every module owned by their home team. However, a certification is necessary for the abstractor to work on any tasks for a particular module.

In circumstances where an abstractor has completed all available tasks for their home team, the abstractor can be temporarily assigned to a loan team (as represented by the arrow 730). The assignment may occur automatically by a controller (for example, the controller 304 of FIG. 3). The abstractor may automatically assigned to the loan team. After the abstractor completed a task for the loan team, the controller may determine whether any tasks are available on the home team. Tasks for the home team are prioritized ahead of any tasks for a loan team.

In some implementations, an abstractor may be temporarily loaned to another team temporary. In some implementations, an abstractor may be manually assigned to a particular module for which they are certified. For example, an abstractor may be temporarily assigned to a lower-priority module, for example, to ensure that work on the lower-priority modules get completed. In some implementations, the abstractor will remain assigned to the module until all tasks for that module are completed. Once all tasks for the module are completed, the abstractor is reassigned to their home team.

In some implementations, an abstractor may be individually assigned to multiple modules on a permanent basis. Tasks for the modules to which the abstractor is individually assigned may take precedence over tasks for their home team.

In some implementations, a controller may automatically rebalance work between teams. For example, the controller may determine that the number of tasks for a particular module exceeds a predetermined threshold. In response to determining that the number of tasks exceeds the threshold, the controller may automatically assign abstractors to the module. In some implementations, the controller may first assign idle abstractors, abstractors from teams that have the least number of tasks, and/or abstractors that have the least number of tasks, weighted by priority. For example, tasks for a high priority module may be given a weight of three, making each of those tasks equivalent to three tasks for a low priority module that have been given a weight of one. The controller may provide an estimate for when work on a particular module may be completed. The estimate may be based on the number of modules currently assigned to various teams, the number of tasks associated with each module, and the priority of the different modules.

Figure 8:
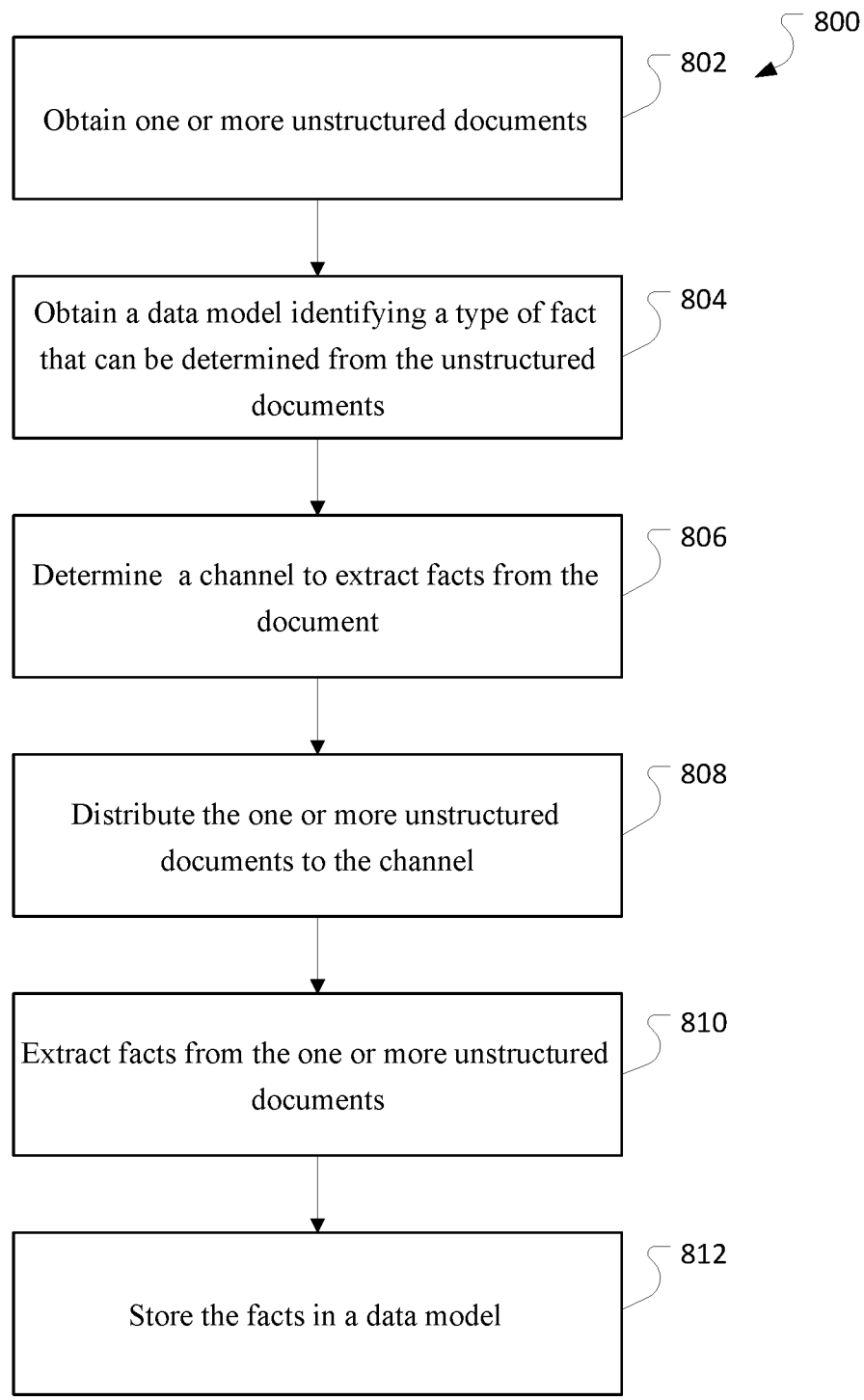
FIG. 8 is a flowchart of an example process 800 for processing electronic medical records.

FIG. 8 is a flowchart of an example process 800 for processing unstructured documents. The process can be performed by a system, for example, the system described in FIG. 3.

The process 800 obtains one or more unstructured documents (802). The unstructured documents may be, for example, electronic medical records.

The process 800 obtains a data model identifying a type of fact that can be determined from the unstructured document (804).

The process 800 determines a channel to extract facts from the documents (806).

The process 800 distributes the unstructured documents to the channel (808).

The process 800 extracts facts from the one or more unstructured documents (810). In some implementations, a cohort of patients may be identified based on the extracted facts.

The process 800 stores the facts in a data model (812). In some implementations, the facts in the data model may be verified using training documents for which the facts are known.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (i.e., one or more modules of computer program instructions, encoded on computer storage mediums for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The computer storage medium can be non-transitory.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example, a programmable processor, a computer, a system on a chip, or multiple ones, or combinations, of the foregoing The apparatus can include special purpose logic circuitry (e.g., an FPGA (field programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application-specific integrated circuit)).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive, data from or transfer data to, or both, one or more mass storage devices for storing data (e.g., magnetic, magneto-optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive)), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back-end component (e.g., as a data server), a middleware component (e.g., an application server), or a front-end component (e.g., a user computer having a graphical user interface or a Web browser through which a user can interact with an implementation of the subject matter described in this specification), or any combination of one or more such back-end, middleware, or front-end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for processing data originating from electronic medical records, comprising:
    obtaining one or more unstructured documents containing facts;
    obtaining, by a computer system, a data model, the data model identifying a plurality of modules, each module including one or more facts that can be determined from the one or more unstructured documents;
    dividing, by the computer system, the one or more unstructured documents into pieces of unstructured data based on the contained facts of the one or more unstructured documents and the included facts of at least one of the plurality of modules;
    determining, by the computer system, corresponding channels to extract facts from the pieces of unstructured data based on the identified modules, wherein at least two of the channels are trained separately from each other;
    distributing, by the computer system, the pieces of unstructured data to the corresponding channels;
    extracting, by the corresponding channels, facts from the pieces of unstructured data; and
    storing the extracted facts in the data model.

2. The computer-implemented method of claim 1, wherein extracting facts is performed by at least one computer system.

3. The computer-implemented method of claim 1, further comprising verifying the extracted facts stored in the data model, wherein the one or more unstructured documents include training documents for which the facts are known.

4. The computer-implemented method of claim 1, further comprising identifying a cohort of patients based on the extracted facts.

5. The computer-implemented method of claim 1, further comprising:
    determining a measure of quality for the extracted facts; and
    updating the data model based on the measure of quality.

6. The computer-implemented method of claim 1, further comprising:
  identifying at least one of the extracted facts as being longitudinal; and
  comparing the at least one fact to previously extracted facts of a same type for a same patient.

7. The computer-implemented method of claim 1, further comprising:
  extracting a set of facts from a set of unstructured documents;
  establishing the set of unstructured documents as a training set;
  training a model using the set of facts and the set of unstructured documents; and
  extracting new facts from new unstructured documents using the model.

8. A system comprising:
  one or more computers and
  one or more storage devices storing instructions that are operable, when executed by the one or more computers, to cause the one or more computers to perform operations comprising:
    obtaining one or more unstructured documents containing facts;
    obtaining, by the one or more computers, a data model, the data model identifying a plurality of modules, each module including one or more facts that can be determined from the one or more unstructured documents;
    dividing, by the one or more computers, the one or more unstructured documents into pieces of unstructured data based on the contained facts of the one or more unstructured documents and the included facts of at least one of the plurality of modules;
    determining, by the one or more computers, corresponding channels to extract facts from the pieces of unstructured data based on the identified modules, wherein at least two of the channels are trained separately from each other;
    distributing, by the one or more computers, the pieces of unstructured data to the corresponding channels;
    extracting, by the corresponding channels, facts from the pieces of unstructured data; and
    storing the extracted facts in the data model.

9. The system of claim 8, wherein extracting facts is performed by at least one computer system.

10. The system of claim 8, wherein the operations further comprise verifying the extracted facts stored in the data model, wherein the one or more unstructured documents include training documents for which the facts are known.

11. The system of claim 8, wherein the operations further comprise identifying a cohort of patients based on the extracted facts.

12. The system of claim 8, wherein the operations further comprise:
  determining a measure of quality for the extracted facts; and
  updating the data model based on the measure of quality.

13. The system of claim 8, wherein the operations further comprise:
  identifying at least one of the extracted facts as being longitudinal; and
  comparing the extracted at least one fact to previously extracted facts of a same type for a same patient.

14. The system of claim 8, wherein the operations further comprise:
  extracting a set of facts from a set of unstructured documents;
  establishing the set of unstructured documents as a training set;
  training a model using the set of facts and the set of unstructured documents; and
  extracting new facts from new unstructured documents using the model.

15. A non-transitory computer storage medium encoded with computer program instructions that when executed by one or more computers cause the one or more computers to perform operations comprising:
  obtaining one or more unstructured documents containing facts;
  obtaining, by the one or more computers, a data model, the data model identifying a plurality of modules, each module including one or more facts that can be determined from the one or more unstructured documents;
  dividing, by the one or more computers, the one or more unstructured documents into pieces of unstructured data based on the contained facts of the one or more unstructured documents and the included facts of at least one of the plurality of modules;
  determining, by the one or more computers, corresponding channels to extract facts from the pieces of unstructured data based on the identified modules, wherein at least two of the channels are trained separately from each other;
  distributing, by the one or more computers, the pieces of unstructured data to the corresponding channels;
  extracting, by the corresponding channels, facts from the pieces of unstructured data; and
  storing the extracted facts in the data model.

16. The non-transitory computer storage medium of claim 15, wherein extracting facts is performed by at least one computer system.

17. The non-transitory computer storage medium of claim 15, wherein the operations further comprise verifying the extracted facts stored in the data model, wherein the one or more unstructured documents include training documents for which the facts are known.

18. The non-transitory computer storage medium of claim 15, wherein the operations further comprise identifying a cohort of patients based on the extracted facts.

19. The non-transitory computer storage medium of claim 15, wherein the operations further comprise:
  determining a measure of quality for the extracted facts; and
  updating the data model based on the measure of quality.

20. The non-transitory computer storage medium of claim 15, wherein the operations further comprise:
  identifying at least one of the extracted facts as being longitudinal; and
  comparing the at least one fact to previously extracted facts of a same type for a same patient.

21. The non-transitory computer storage medium of claim 15, wherein the operations further comprise:
  extracting a set of facts from a set of unstructured documents;
  establishing the set of unstructured documents as a training set;
  training a model using the set of facts and the set of unstructured documents; and
  extracting new facts from new unstructured documents using the model.

22. The non-transitory computer storage medium of claim 15, wherein the corresponding channels are configured to extract facts from the pieces of unstructured data in parallel.

23. The non-transitory computer storage medium of claim 15, wherein the operations further comprise training a machine learning model to tag documents based on the stored extracted facts.

24. The non-transitory computer storage medium of claim 15, wherein:
- at least one of the corresponding channels is an automated channel configured to automatically extract facts;
- at least one of the corresponding channels is a semi-automated channel configured to extract facts with partial human interaction; and
- the pieces of unstructured data are distributed to the corresponding channels based on a type of fact to be extracted.

25. The non-transitory computer storage medium of claim 15, wherein:
- at least one piece of unstructured data is distributed to multiple corresponding channels, each of the multiple corresponding channels extracting at least one fact; and
- the operations further comprise comparing the facts extracted by the multiple corresponding channels.

* * * * *